United States Patent [19]

Day et al.

[11] Patent Number: 5,444,160
[45] Date of Patent: Aug. 22, 1995

[54] ACETYLATED ALGINATES, AND METHOD FOR PRODUCING ACETYLATED ALGINATES

[75] Inventors: Donal F. Day; Jin W. Lee, both of Baton Rouge, La.

[73] Assignee: Board of Supervisors of Louisiana State University and Agricultural and Mechanical College, Baton Rouge, La.

[21] Appl. No.: 233,135

[22] Filed: Apr. 26, 1994

Related U.S. Application Data

[62] Division of Ser. No. 943,914, Sep. 11, 1992, Pat. No. 5,308,761.

[51] Int. Cl.$^6$ ............................................. C08B 37/04
[52] U.S. Cl. ........................................................ 536/3
[58] Field of Search ..................... 536/3, 124; 435/101, 435/252.34, 874

[56] References Cited

U.S. PATENT DOCUMENTS

| | | | |
|---|---|---|---|
| 3,856,625 | 12/1974 | Imrie | 195/31 P |
| 3,905,869 | 9/1975 | Hidaka et al. | 435/221 |
| 4,235,966 | 11/1980 | Jarman et al. | 435/101 |
| 4,490,467 | 12/1984 | Jarman et al. | 435/101 |

OTHER PUBLICATIONS

Gross et al., "Studies on the Extracellular Polysaccharides (EPS) Produced in vitro by Pseudomonas phaseolicola. II. Characterization of Levan, Alginate, and 'LPS'," J. Phytopathol., vol. 119, No. 3, pp. 206–215 (1987).
Skjåk-Bræk et al., "Selective Acetylation of Mannuronic Acid Residues in Calcium Alginate Gels," Carbohydrate Research, vol. 185, pp. 119–129 (1989).
Gross et al., "Demonstration of Levan and Alginate in Bean Plants (Phaseolus vulgaris) Infected by Pseudomonas syringae pv. phaseolicola," J. Phytopathol., vol. 120, No. 1, pp. 9–19 (1987).
Skjåk-Bræk et al., "Monomer Sequence and Acetylation Pattern in Some Bacterial Alginates," Carbohydrate Research, vol. 154, pp. 239–250 (1986).
Gross et al., "Studies on the Extracellular Polysaccharides (EPS) Produced in vitro by Pseudomonas phaseolicola. I. Indications for a Polysaccharide Resembling Alginic Acid in Seven P. syringae Pathovars," J. Phytopathol. vol. 118, No. 3, pp. 276–287 (1987).
Pindar et al., "The Biosynthesis of Alginic Acid by Azotobacter vinelandii," Biochem. J., vol. 152, pp. 616–622 (1975).
Gross et al., "Studies on the Extracellular Polysaccharides (EPS) Produced in vitro by Pseudomonas phaseolicola. III. Kinetics of Levan and Alginate Formation in Batch Culture and Demonstration of Levansucrase Activity in Crude EPS," J. Phytopathol., vol. 119, No. 4, pp. 289–297 (1987).

Primary Examiner—Nathan M. Nutter
Attorney, Agent, or Firm—John H. Runnels

[57] ABSTRACT

A novel method of biosynthetically acetylating seaweed alginates by modification with certain Pseudomonas syringae, such as P. syringae subsp. phaseolicola, is disclosed. The acetylated seaweed alginates thus produced are also novel. Acetylation occurs almost entirely in the O-2 and O-3 positions of the mannuronic acid residues. The acetylated alginates have several desirable properties. For example, acetylation increases the polymers' viscosity; it increases the flexibility of their gels; and it can produce a strong, thermoreversible-gel network. Acetylation increases the viscosity of the polymer, decreases ion-binding capacity, and decreases the ability to gel with calcium. The degree of acetylation can be controlled by controlling the exposure time, which allows the properties of the resulting polymer to be custom-made. Thus the properties of the polymer can be tailored to the intended end-use.

1 Claim, No Drawings

ACETYLATED ALGINATES, AND METHOD FOR PRODUCING ACETYLATED ALGINATES

This is a divisional of application Ser. No. 07/943,914, filed Sep. 11, 1992 and now U.S. Pat. No. 5,308,701 the entire disclosure of which is incorporated by reference.

This invention pertains to novel acetylated alginates, and to a novel method of making acetylated alginates through the modification of seaweed alginate by certain microorganisms.

Alginates are a class of naturally occurring polysaccharides found primarily in marine brown algae, the Phaeophyceae. Alginate-like polymers are also produced by a few bacteria such as *Azotobacter vinelandii* and several species of *Pseudomonas*, such as *Pseudomonas aeruginosa* and some strains of *Pseudomonas syringae*.

Alginatesmay be extracted from seaweeds by means which are well known in the art. Naturally occurring seaweed-derived alginates are typically block copolymers of $\beta$-D-mannuronic acid and its C-5 epimer, $\alpha$-L-guluronic acid. Unmodified seaweed-derived alginates will gel in the presence of salts, and have many established uses. Among the useful properties of alginates are their water-holding capacity; their ability to gel; their usefulness as emulsifiers; and their usefulness as stabilizers. As just some of many examples, alginates are used as food thickeners and stabilizers; calcium alginate gel beads are used to immobilize bacteria or other cells used in biological processes or fermentations; and alginate gels show promise as a substrate for biomedical implants. See generally Cottrell et al., "Alginates", Chapter 2 in Davidson (Ed.), Handbook of Gums & Resins; Cottrell et al., "Alginic Acid," Chapter 5 (pp. 99-126) in Chemistry and Enzymology of Marine Algal Polysaccharides (1967); Sandford et al., "Industrial Utilization of Polysaccharides," Chapter 7 in The Polysaccharides, Vol. 2 (Aspinall, Ed.) (1983); and Skják-Bræk, "Alginates: Biosyntheses and Some Structure-Function Relationships Relevant to Biomedical and Biotechnical Applications," Biochemical Society Transactions, vol 20, pp. 27-33 (1992) (not admitted to be prior art); the entire disclosures of each of which are incorporated by reference.

Seaweed alginates do not naturally occur in an acetylated form. No prior reference suggests a biosynthetic route for acetylating a seaweed alginate.

Although the bacterial alginate-like polymers often occur in an acetylated form, the structures of their polysaccharide backbones are substantially different from those of seaweed alginates. Seaweed alginates are typically block copolymers of mannuronic and guluronic acid residues; i.e., they are composed of alternating homopolymeric sequences of mannuronic acid residues and guluronic acid residues. Current research indicates that, contrary to some earlier reports, bacterial alginate-like polymers are not block copolymers. Rather, the bacterial polymers appear to be composed of random sequences of mannuronic and guluronic acid residues. Many of the mannuronic acid residues in the bacterial polymers are naturally acetylated. By contrast, seaweed alginates do not naturally occur in acetylated form.

U.S. Pat. Nos. 4,235,966 and 4,490,467 discuss the production of partially-acetylated, bacterial, alginate-like polymers by fermenting *Pseudomonas* strains in nutrient media. The U.S. Pat. No. 4,235,966 patent lists *P. syringae* as a possible species to use in the process, although the particular examples all use other *Pseudomonas* species. U.S. Pat. No. 3,856,625 discusses the production of a partially-acetylated, bacterial, alginate-like polymer by fermenting *Azotobacter vinelandii* in a culture medium. Although these earlier patents and other earlier work sometimes refer to the bacterial polymers as block copolymers of mannuronic and guluronic acid residues, more recent work shows that the bacterial alginate-like polymers are actually composed primarily of random sequences of mannuronic and guluronic acid residues; or stated differently, that they have a relatively small proportion of homopolymeric sequences when compared with the algal alginates. See, e.g., Skják-Bræk et al., "Monomer Sequence and Acetylation Pattern in Some Bacterial Alginates," Carbohydrate Research, vol. 154, pp. 239-250 (1986); and Pindar et al., "The Biosynthesis of Alginic Acid by *Azotobacter vinelandii*," Biochem. J., vol. 152, pp. 616-622 (1975).

Skják-Bræk et al., "Selective Acetylation of Mannuronic Acid Residues in Calcium Alginate Gels," Carbohydrate Research, vol. 185, pp. 119-129 (1989) reported the chemical acetylation of a seaweed alginate by acetic anhydride. Acetylation in the product was observed in both mannuronic and guluronic acid residues, with acetylation of the mannuronic acid residues predominating.

A novel method of biosynthetically acetylating seaweed alginates to produce acetylated seaweed alginates has been discovered. The acetylated seaweed alginates thus produced are also novel. Acetylation in accordance with the present invention occurs almost entirely in the O-2 and O-3 positions of the mannuronic acid residues. No acetylation occurs on the guluronic acid residues.

Acetylation of the seaweed alginates has been found to confer desirable properties to the alginates. For example, acetylation increases the polymers' viscosity; it increases the flexibility of their gels; and it can produce a strong, thermoreversible-gel network. Acetylated alginates in accordance with the present invention may be used anywhere alginates are Currently used, generally with greater efficiency. On a comparable-weight basis, the acetylated alginates of the present invention will yield higher viscosities. They may be used in calcium-ion-containing products, because they will not sequester the calcium ions as non-acetylated alginates typically will. They are also more resistant to degradation, and will generally be more useful where temperature, stability, or the amount of material added is important.

It has been unexpectedly discovered that seaweed alginates may be modified by certain *Pseudomonas syringae*, such as *P. syringae* subsp. *phaseolicola*, resulting in the acetylation of the seaweed alginate. The degree of acetylation can be controlled by controlling the exposure time or the concentration of the carbon source, thus allowing the properties of the resulting polymer to be custom-made. Acetylation increases the viscosity of the polymer, decreases ion-binding capacity, and decreases the ability to gel with calcium. Thus the properties of the polymer can be tailored to the intended end-use.

This result is unexpected, as there are very few bacteria which will grow on seaweed alginates. Most microorganisms cannot use such alginates as a carbon source, and would therefore not be expected to use alginates in their metabolic pathways. The few bacteria known to use alginates as a carbon source are all marine microorganisms. *Pseudomonas syringae*, a terrestrial plant pathogen which attacks green peas, does not appear to use seaweed alginate as a carbon source. The seaweed alginate does not appear to be used as a feedstock by the microorganisms, even when used in the process of the present invention. The microorganisms act, in effect, as a type of biological catalyst for the acetylation reaction.

One embodiment of this invention comprises the acetylation of seaweed alginate by a *Pseudomonas syringae*, such as *P. syringae* subsp. *phaseolicola*. Although the novel process has not yet been tried in other strains or species, it is expected that it will also work with other strains of *Pseudomonas syringae*. While it will probably also work in the other *Pseudomonas* species that make alginate-like polymers, all other known *Pseudomonas* species making such polymers are human pathogens, and therefore would preferably be avoided. Again, while the process may also work in *Azotobacter vinelandii*, that bacterium would not be preferred, as it makes its alginate-like polymer, and the enzyme or enzymes to acetylate it, only during a limited portion of its life cycle, namely when it is sporulating. Preferred bacteria for use in the present invention should be non-pathogenic, and should produce the acetylation enzyme or enzymes constitutively, or at least during a large portion of the life cycle. To date, only *Pseudomonas syringae* is known to meet both of these criteria.

Three variations of this basic technique have been used to date: (1) batch fermentation of free cells of *P. syringae* with an appropriate carbon source, followed after a time by the addition of seaweed alginate to the culture medium; (2) continuous fermentation of free cells, with continuous feeding of seaweed alginate and an appropriate carbon source; and (3) continuous reaction using immobilized cells, with continuous feeding of seaweed alginate and a carbon source.

In all the Examples below, the *Pseudomonas syringae* subsp. *phaseolicola* was obtained from the American Type Culture Collection, Rockville, Md., a publicly available strain having accession number ATCC 19304. The process of this invention would also be expected to work with many mutants, recombinants, or genetically engineered derivatives of this strain or of other *Pseudomonas syringae* strains, or of the progeny of any of these strains; or strains which are the progeny of any of these strains; provided that the acetylation enzyme activity of *Pseudomonas syringae* is preserved. As used herein, the "acetylation enzyme activity of *Pseudomonas syringae*" denotes enzymatic acetylation activity towards seaweed alginates which is substantially the same as that of *Pseudomonas syringae* subsp. *phaseolicola*, resulting from substantially the same enzyme or enzymes as produced by that strain.

EXAMPLE 1

Each culture was maintained on Pseudomonas Agar P (Difco Laboratories, Detroit). The basic growth medium used comprised an aqueous solution of the following ingredients, with concentrations in g/l given in parentheses: $KH_2PO_4$ (4.0), $Na_2HPO_4$ (6.8), $MgSO_4$ (0.2), $(NH_4)_2SO_4$ (0.5), NaCl (0.4), $KNO_3$ (9.1), and a carbon source such as glycerol, gluconic acid, fructose, or glucose (20.0). Gluconic acid is a preferred carbon source. The pH of the medium was adjusted to 6.6–7.0 prior to sterilization. To inoculate precultures, fresh cells from the agar plates were transferred to 50 ml of the growth medium in 250 ml Erlenmeyer flasks, and incubated for 2 days at 30° C on a rotary shaker at 160 rpm.

Batch fermentation of *Pseudomonas syringae* subsp. *phaseolicola* in the above growth medium was followed by the addition of seaweed alginate to the culture medium at a pH between 6.0–7.0, at a temperature of 30° C., with appropriate aeration and stirring. Fermentation was carried out in a Bench-Top MultiGen (New Brunswick Scientific Co., New Brunswick, N.J.) with a working volume of 400 ml. Seaweed alginate was added to the culture broth late in the logarithmic growth phase, at a concentration between 300–2,000 μg/ml. The fermentation continued 3–4 days after the addition of seaweed alginate. The final degree of acetylation obtained from the culture broth was between 5–50%. The degree of acetylation was observed to increase with increasing concentration of gluconic acid when the concentration of alginate was about 800 μg/ml.

The amount of alginate was determined by the method of Blumenkrantz et al., "New Method for Quantitative Determination of Uronic Acid," Analytical Biochemistry, vol. 54, pp. 484–489 (1973), the disclosure of which is incorporated by reference. The degree of acetylation was determined by the method of McComb et al., "Determination of Acetyl in Pectin and in Acetylated Carbohydrate Polymer: Hydroxamic Acid Reaction," Analytical Chemistry, vol. 29, pp. 819–821 (1957), the disclosure of which is incorporated by reference.

EXAMPLE 2

The microorganisms and initial cultivation were as described in Example 1. *Pseudomonas syringae* subsp. *phaseolicola* was continuously fermented with a continuous feeding of seaweed alginate and carbon source. The continuous fermentation process comprised growing a culture of *Pseudomonas syringae* subsp. *phaseolicola* on the growth medium described in Example 1 at a pH between 6.0–7.0; at a temperature of 30° C.; with appropriate aeration; and with the continuous feeding of seaweed alginate, 0.1M phosphate buffer (pH 6.0 or 7.0), and the carbon source. The concentration of seaweed alginate was 300–2,000 μg/ml, and the carbon source was 0.5%–2.0% by weight. Acetylated alginate with an acetylation degree of 15–30% was continuously recovered, the degree of acetylation being dependent on the concentration of the carbon source added and the dilution rate of alginate.

EXAMPLE 3

The microorganisms and initial cultivation were as described in Example 1. Immobilized *Pseudomonas syringae* subsp. *phaseolicola* were prepared. When the *Pseudomonas syringae* subsp. *phaseolicola* culture reached the stationary phase, the cells were harvested and washed with distilled water. About 5 g wet weight of cells were suspended in 10 ml of distilled water and chilled in ice. A chilled 10 ml solution of 0.02M potassium phosphate buffer, pH 7.0, containing 2.85 g acrylamide, 0.15 g N,N'-methylene-bis-acrylamide, 10 mg ammonium persulphate, and 10 μl of a 10 mg/ml solution of tetramethylethylenediamine was mixed with the prepared cell suspension. The chilled buffer/cell suspension was poured into glass Petri dishes and covered. After polymerization (about one hour), the gel was sieved and suspended in 100 ml of 0.02M potassium phosphate buffer, pH 7.0, allowed to settle, and the fines decanted.

The process of the continuous modification of alginate of Example 2 was used, except that immobilized cells were used instead of free cells. The modification was carried out in a 700 ml Kontes Airlift Bioreactor (Kontes Life Sciences Products, Vineland, N.J.). The total system lasted longer than that of Example 2. During more than 20 days of continuous operation, acetylated alginate with an acetylation degree of 10–25% was continuously recovered, the degree of acetylation being dependent on the concentration of the carbon source and the dilution rate of alginate.

EXAMPLE 4

The microorganisms and initial cultivation were as described in Example 1. Immobilized *Pseudomonas syringae* subsp. *phaselicola* were prepared. When the *Peudomonas syringae* subsp. *phaseolicola* cultures reached the early stationary phase, the cells were harvested and washed with distilled water. About 10 g wet weight of cells were suspended in a 500 ml solution of sterilized phosphate buffer (Potassium phosphate monobasic, 4.0 g/l; sodium phosphate dibasic, 6.8 g/l; pH 6.8) containing 25 g activated carbon. To promote the adsorption of the bacteria onto the surface of the activated carbon, this mixture was incubated overnight at 4° C. Following this incubation, the supernatant was discarded and the carbon particles were used as the source of immobilized cells. Otherwise, the process for the continuous modification of alginate described in Example 3 was followed. The acetylated alginate was continuously recovered, the degree of acetylation being dependent on the concentration of the carbon source and the dilution rate of alginate. The degree of acetylation reached was up to 100% of the mannuronic acid residues in the alginate.

Selectivity of Acetylation

Proton nuclear magnetic resonance (NMR) spectra confirmed that the acetylated alginates produced in the above Examples were different from any chemical structures previously reported. The NMR spectra showed that the alginates were acetylated quite selectively, the acetylation occurring almost entirely at the O-2 and O-3 positions of the mannuronic acid residues.

The acetylated alginates of the present invention differ from the acetylated, alginate-like polymers naturally produced by some bacteria in that the acetylated alginates of the present invention comprise copolymers of blocks of mannuronic acid residues and blocks of guluronic acid residues. By contrast, the mannuronic acid and guluronic acid residues of the bacterial polymers are distributed more randomly. Furthermore, bacterial alginate-like polymers are not approved for food uses; and in contrast to the acetylated alginates of the present invention, the bacterial polymers do not readily gel or bind salts.

The acetylated alginates of the present invention differ from naturally occurring seaweed alginates in that the latter are not acetylated.

The acetylated alginates of the present invention differ from previously reported seaweed alginates which have been chemically acetylated, in that the latter are acetylated in both mannuronic acid residues and guluronic acid residues; while the acetylated alginates of the present invention are acetylated almost entirely at the O-2 and O-3 positions of the mannuronic acid residues. Furthermore, chemically acetylated alginates are not commonly prepared because of the toxicity of the process involved.

We claim:

1. A composition of matter consisting essentially of a copolymer of blocks of homopolymeric mannuronic acid residues and blocks of homopolymeric guluronic acid residues; wherein 5% to 100% of the mannuronic acid residues are acetylated at the O-2 position, at the O-3 position, or at both the O-2 and O-3 positions; and wherein substantially all of the guluronic acid residues are not acetylated.

* * * * *